United States Patent [19]
Taylor

[11] Patent Number: 5,301,679
[45] Date of Patent: Apr. 12, 1994

[54] METHOD AND SYSTEM FOR ANALYSIS OF BODY SOUNDS

[75] Inventor: Colin R. Taylor, New York, N.Y.

[73] Assignee: Taylor Microtechnology, Inc., New York, N.Y.

[21] Appl. No.: 708,748

[22] Filed: May 31, 1991

[51] Int. Cl.$^5$ .............................................. A61B 7/00
[52] U.S. Cl. ..................... 128/773; 128/715
[58] Field of Search .............. 128/773, 774, 780, 715

[56] References Cited

U.S. PATENT DOCUMENTS

| | | | |
|---|---|---|---|
| 4,792,145 | 12/1988 | Eisenberg et al. | 128/773 |
| 4,928,705 | 5/1990 | Sekhar et al. | 128/773 |
| 4,991,581 | 2/1991 | Andries | 128/773 |
| 5,010,889 | 4/1991 | Bredesen et al. | 128/773 |
| 5,035,247 | 7/1991 | Heiman | 128/773 |

Primary Examiner—Max Hindenburg
Attorney, Agent, or Firm—Helfgott & Karas

[57] ABSTRACT

A method and a system for evaluation of a human disease by recording body sounds for extended periods of time by a microphone placed in contact with the body of the patient and using computer processing of body sound data to provide frequency domain and time domain sound amplitudes. A computer reads out a converted measurement of a sound taken by the microphone and places the data on the computer data bus for further processing. The method and system provide a diagnostic information on diseases, such as certain diseases of the gastro-intestinal tract and the heart, which generate abnormal body sounds and provide assessment of patient progress during treatment of such disease entities.

9 Claims, 6 Drawing Sheets

METHOD AND SYSTEM FOR ANALYSIS OF BODY SOUNDS

BACKGROUND OF THE INVENTION

1. Field of the Invention

This invention relates to a method and system for computer analysis of body sounds derived from the muscular activity of various body organs or systems, and to use of such method and system in diagnosing and monitoring activity of diseases and syndromes associated with abnormal sound production.

2. Description of the Prior Art

The stethoscope has been used for evaluation of human disease since the 18th Century. Auscultation is performed by placing the stethoscope on the skin overlying human structures such as heart, abdomen, lungs, or blood vessels, and allows the physician to hear body sounds in the frequency range of human hearing. However, the stethoscope does not allow evaluation of sounds in the low frequency range not heard by the human ear ("infrasound"), and only permits real-time, audible evaluation of body sounds.

Phonocardiography is an established technique for converting heart sounds within the auditory range into electrical energy using a microphone, followed by oscilloscopic or paper visual display of heart sounds within the time domain. Apex cardiography is also an established technique somewhat similar to phonocardiography except that it deals with low frequency vibrations in the infrasonic range. Some physicians or trained personnel have performed limited evaluation of computer processing of heart sound data (phonocardiography and apex cardiography) as described, for example, in "Computer Analysis Techniques for Phonocardiogram Diagnosis" published in "Computers and Biomedical Research", by Sarkady A. A. Clark R. L. and Williams R, 9, 349–363, 1976 or in "Recording of the Fourth Heart Sound by the Signal Averaging Method", by Yanaga et al, Jap. Heart J., May 1977, 340–347. However, these techniques have not been utilized for evaluation of the diagnostic utility of abnormal sound generation in other body systems, such as evaluation of abnormal bowel sounds.

SUMMARY OF THE INVENTION

It is an object of the present invention to provide a physician or any other trained personnel with a detailed computer-analyzed information on the muscular activity of various body organs derived from body sounds.

In accordance with the present invention, a method and a system for computer analysis of body sounds are provided, in which body sounds are recorded and analyzed by placing a microphone on the body surface or inserting a microphone within the body (e.g. oral insertion or rectal insertion into the gastro-intestinal tract), converting the body sounds recorded by the microphone into an electrical signal which is amplified and transmitted to a spectrum analyzer either directly or via conventional magnetic tape recording of sound, separating the sound energy into various frequency bands in the spectrum analyzer, calculating "envelope" amplitudes for each frequency band, and computer processing of the data obtained for diagnosis of certain disease conditions and for monitoring of patient progress.

The aforementioned objects, features and advantages of the invention will, in part, become obvious from the following more detailed description of the invention, taken in conjunction with the accompanying drawing, which form an integral part thereof.

DETAILED DESCRIPTION OF THE PREFERRED EMBODIMENTS

As previously mentioned, sounds emanating from various body organs or structures may be of value in evaluating human disease. The method and system according to the present invention provides a novel method for recording sound signals over extended time periods, and for computer processing of such data.

Figure 1:
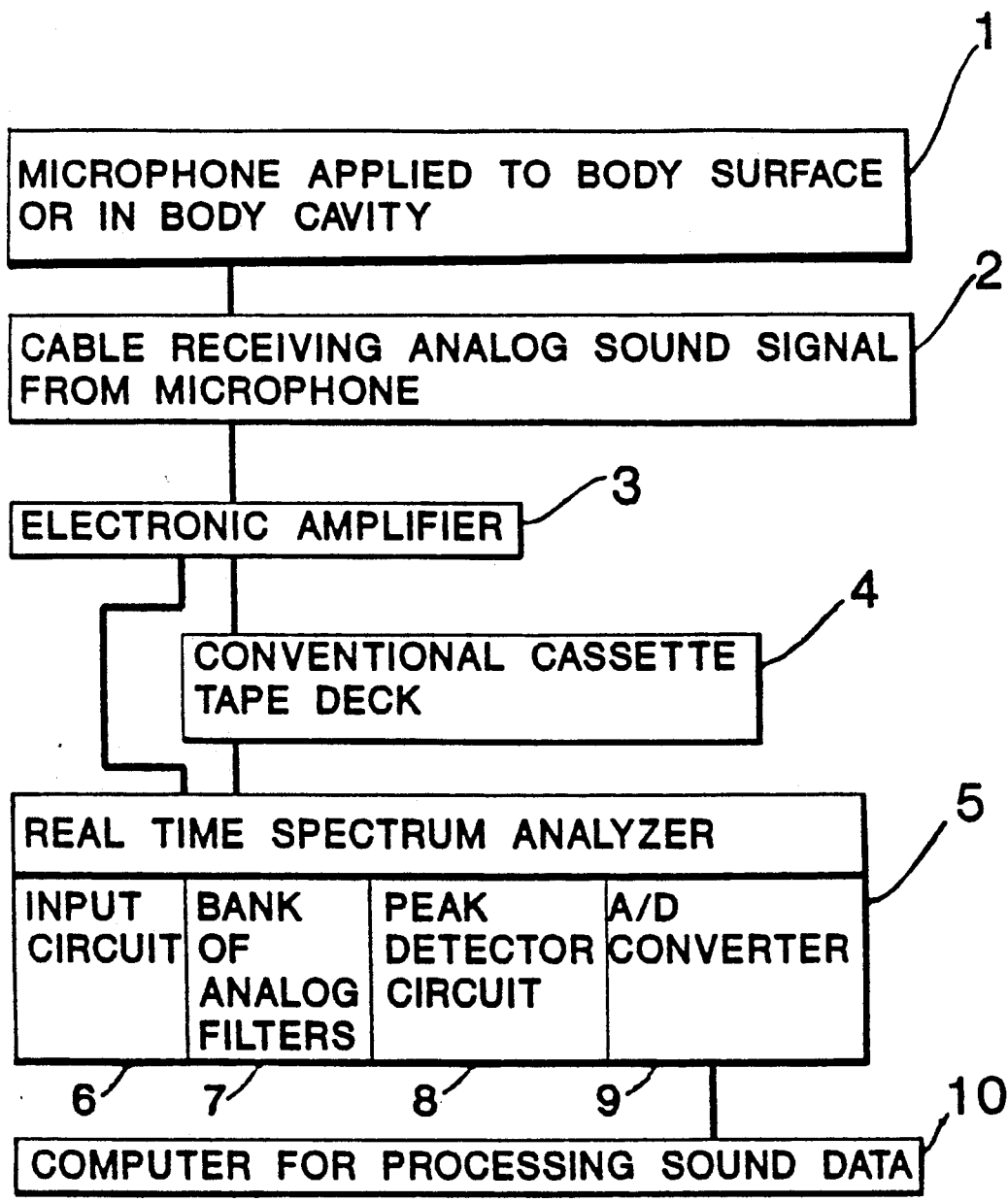
FIG. 1 is a block diagram of an embodiment of the system according to this invention.

FIG. 1 is a block diagram of the system of a preferred embodiment of the present invention. Block 1 is a microphone (e.g. a piezoelectric transducer) which is applied to the body surface or placed in a body cavity. Block 2 represents a cable receiving an analog sound signal from the microphone. Block 3 represents an electronic amplifier. The sound energy converted into electrical energy in the microphone 1 is transmitted to amplifier 3, from which an amplified signal is supplied either to a conventional cassette tape deck 4 with adequate frequency response or directly to block 5. Block 5 represents a real-time spectrum analyzer which is constructed to divide the sound signal received therein into frequency bands and calculate the "envelope" amplitude for each band. The spectrum analyzer utilized in the system of the present invention is of a commercially available type, for example, a real-time audio ⅓ octave spectrum analyzer manufactured by Eventide Clockworks Inc. The real-time ⅓ octave radio spectrum analyzer may be model APX 252 designed to be installed directly in any Apple II computer I/O slot. The analyzer is compatible with the Apple II ® family of computers. Complete machine language software for interactive real-time analysis is contained in 5K bytes of onboard EPROM memory. The analyzer allows extremely rapid and versatile analysis of virtually any audio signal. Access to analyzer functions is made via high-level commands that are issued from the keyboard or within Basic or machine language programs. The spectrum analyzer 5 comprises an input cable or circuit 6 for inputting an amplified sound signal supplied directly from amplifier 3 or from a prerecorded tape signal from the cassette tape deck 4, a bank of analog filters 7 which divides the sound signal received therein into frequency bands of ⅓ octave width, a peak detector circuit 8 using a diode detector which allows calculation of the "envelope" amplitude and stores the analog value in a capacitor, and an analog-to-digital converter 9 which scans the output from each frequency band and converts the analog values into digital values. Block 10 represents a computer which reads out a converted sound amplitude measurement from the A/D converter output which places the data on the computer data bus for further processing.

The computer may be a part of the spectrum analyzer or be any conventional personal computer connected to a spectrum analyzer. For example, an Apple IIe ® personal computer (Apple Computer Inc., Cupertino, Calif.) with a Microbuffer graphic printer interface and an Apple ® dot matrix printer may be used. It is, of course, understandable that any other type of a personal computer may be utilized.

Computer program listings (computer algorithms) below have been used for the computer analysis of body sounds according to the invention.

Thus, according to the method of this invention, sound is measured by the microphone (e.g. a piezoelectric transducer capable of low frequency response applied to the body surface or inserted into the rectum). When the microphone is applied to the body surface, constant pressure is applied either by a manual applicator or by a strap which holds the microphone in place; adequate reproducibility of sound amplitude measurement is obtained provided the application pressure exceeds 500 grams.

The electric signal of recorded sound is amplified and may then be transmitted directly to the spectrum analyzer 5 via an electronic interface, or recorded on conventional cassette tape deck 4. When a cassette tape deck is used, some reproducible attenuation of the sound signal occurs, especially in the infrasound component of the signal, but still allows intra-patient and inter-patient comparisons.

The analog signal is digitized using the analog-to-digital converter 6, divided into "envelope" amplitudes for various frequency bands. In one embodiment of this invention, the sound signal is divided into ⅓ octaves by an analog filter bank. In another embodiment of this invention, frequency analysis of the sound signal is provided by Fast Fourier Transformation analysis. The unprocessed amplitude/frequency data is stored in the computer (e.g. a personal microcomputer).

Subsequent computer analysis of the data is dependent on the disease or syndrome under study, as described in the following examples.

EXAMPLE 1

Analysis of Bowel Sounds

Conventional stethoscopic examination of bowel sounds is usually performed for only a few seconds, and the sound data is not stored to allow quantitative comparisons. Bowel sounds are highly variable over short time periods, so that stethoscopic examination permits identification of only gross departures from normality (e.g. the pronounced bowel sounds of intestinal obstruction or the absent bowel sounds of paralytic ileus). No automated recording or computer analysis has hitherto demonstrated the diagnostic utility of bowel sound data.

The present invention permits a permanent record of bowel sounds throughout the infrasonic and audible sound spectrum for extended time periods, and permits sophisticated computer processing of the data. The computer processing includes generation of time plots of amplitude at various frequency bands, identification of bowel sound surges using template algorithms, average wave form analysis of bowel sound surges, and average amplitude calculation over extended time periods. Accordingly, this invention markedly enhances the information content obtained from bowel sound evaluation.

TABLE 1

| AMPLITUDE OF BOWEL SOUNDS IN NORMALS, PATIENTS WITH IRRITABLE BOWEL SYNDROME, AND PATIENTS WITH PARALYTIC ILEUS | | | | | |
|---|---|---|---|---|---|
|  | 20–40 HZ | 50–100 HZ | 125–250 HZ | 315–630 HZ | 800–1600 HZ |
| MEAN AMPLITUDE: | | | | | |
| NORMALS (n = 5) | 2.3 ± 0.8 | 2.7 ± 0.5 | 0.63 ± 0.3 | 0.06 ± 0.05 | 0.00 ± 0.00 |
| IBS (n = 3) | 3.8 ± 0.5 | 4.4 ± 0.3 | 1.1 ± 0.3 | 0.17 ± 0.06 | 0.00 ± 0.00 |
| PARALYTIC ILEUS (n = 2) | 0.0 ± 0.0 | 0.0 ± 0.0 | 0.0 ± 0.0 | 0.00 ± 0.00 | 0.00 ± 0.00 |
| PEAK AMPLITUDES: | | | | | |
| NORMALS (n = 5) | 3.9 ± 0.4 | 3.8 ± 0.6 | 3.6 ± 1.3 | 0.55 ± 0.50 | 0.00 ± 0.00 |
| IBS (n = 3) | 6.2 ± 0.2 | 6.3 ± 0.2 | 6.0 ± 1.2 | 1.33 ± 0.25 | 0.00 ± 0.00 |
| PARALYTIC ILEUS (N = 2) | 0.0 ± 0.0 | 0.0 ± 0.0 | 0.0 ± 0.0 | 0.00 ± 0.00 | 0.00 ± 0.00 | values are standard amplitude units for the recording and amplification system and are derived from 20 minute tracings in each patient. They represent the arithmetic mean ± one standard error of the mean. Peak amplitude statistics are based on analysis of consecutive 0.5 second periods throughout the tracing for each patient. Paralytic ileus data is after application of artefact reduction algorithm for body movement, respiratory sounds, and heart sounds.

Table 1 represents the sound amplitudes in three groups of patients—normal volunteers, patients with irritable bowel syndrome, and patients with post-operative paralytic ileus following abdominal surgery. The patients with irritable bowel syndrome had typical incapacitating IBS symptoms of gastro-intestinal irritability over at least a 5-year time period, without evidence of other gastro-intestinal pathology; these patients showed substantially larger sound amplitudes than normals throughout the range of frequency of bowel sounds (20–630 Hz), suggesting increased motility of the gastro-intestinal tract. In contrast, patients with post operative paralytic ileus showed a complete absence of bowel sounds, indicating paralysis of the smooth muscle of the gastro-intestinal tract in response to surgical trauma.

Figure 2:
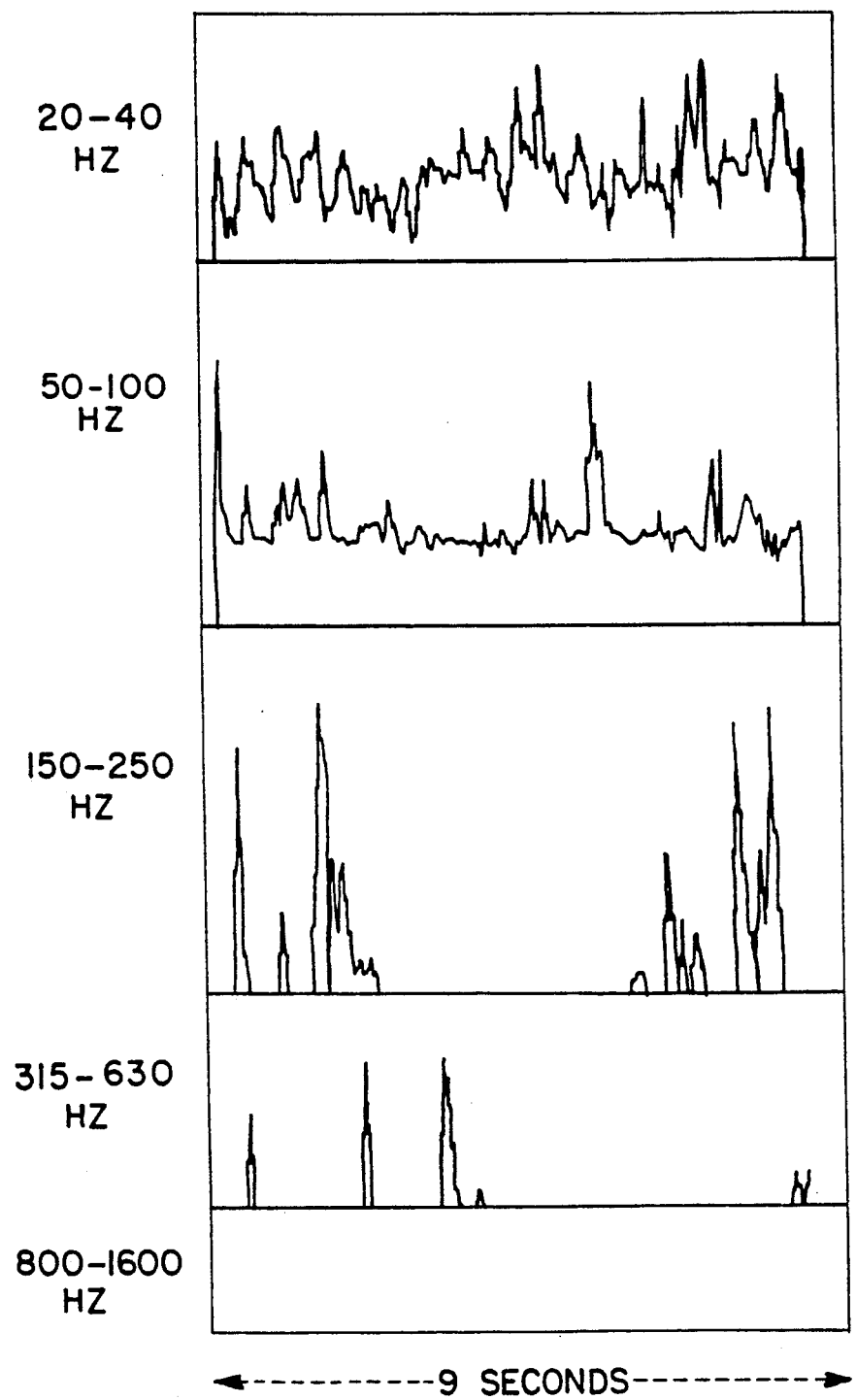
FIG. 2 represents a recording of bowel sounds from a patient with irritable bowel syndrome.

FIG. 2 shows the sound amplitude/time plots in a representative patient with irritable bowel syndrome.

The sound amplitudes are shown on the ordinate and time on abscissa. Numberica values are in standard amplitude units (for recording and amplification system used) and represent statistics (arithmetic average, standard deviation, and standard error or mean) for consecutive 0.5 second periods for an average amplitude/period ("MEAN") and a peak value for a period ("PEAK").

For the amplitude 20–40 HZ: MEAN=3.9 (SD 1.0, SEM 0.3) and PEAK=6.1 (SD 1.5, SEM 0.4).

For 50–100 HZ: MEAN=4.5 (SD 0.8, SEM 0.2) and PEAK=6.4 (SD 2.6, SEM 0.7)

For 125–250 HZ: MEAN=1.0 (SD 1.4, SEM 0.4) and PEAK=5.5 (SD 5.7, SEM 1.6).

| For 315–630 HZ: | MEAN = 0.2 (SD 0.4, SEM 0.1) and PEAK — 1.3. |
|---|---|
| S1: 55.9 | S3: 0 (±0) |
| S2: 54.7 | S4: 35 (±1.4) |
| For 800–1600 HZ: | MEAN = (SD 0.0, SEM 0.0) and PEAK = 0.0 (SD 0.0, SEM 0.0). |

The bulk of the sound energy emanating from the gut is in the 20–40 Hz and 50–100 Hz range with a constant sound level together with additional sound spikes superimposed on this underlying pattern; this contrasts with normal patients who show a lower constant sound level, and a less prominent spiking pattern. The recordings of the 150–250 Hz and 315–630 Hz ranges show an absence of sound during most of the recording, with occasional spikes occurring during the recording; in normal patients in these frequency ranges there is a similar absence of sound during most of the recording and less frequent and prominent spikes.

The applications of the present invention for bowel sound analysis include:

a) Evaluation of return of bowel function in the post-operative period: Following major surgery, there is normally a period of time during which the bowel musculature is temporarily paralyzed; accordingly, normal propagation of bowel contents is prevented, and intravenous feeding is required. This invention permits sensitive identification of return of normal bowel motion, and accordingly may serve as a guide in determining when oral feeding may resume post-operatively.

b) Evaluation of patients with Irritable Bowel Syndrome (IBS): IBS is an ill-defined entity which "is the most common gastrointestinal disease in clinical practice and ... causes great distress to those afflicted and a feeling of helplessness and frustration for the physician attempting to treat it" (Isselbacher and May, 1977). Although the symptoms of IBS may be debilitating, techniques for objective evaluation of the disorder involve uncomfortable and expensive manometric or electromyographic assessment. Accordingly, the diagnosis is usually made on the basis of the patient's history and no convenient procedures are available for either definitive diagnosis or serial evaluation of the effects of therapy. Since IBS is associated with abnormal bowel motility, which may be evaluated by bowel sound evaluation, this invention can provide a simple method to aid in diagnosis and serial evaluation of IBS patients.

EXAMPLE 2

Analysis of Heart Sounds

A number of cardiac diseases are associated with abnormality of sounds emanating from the heart. Examples of abnormal sounds include: third heart sound (S3), fourth heart sound (S4), systolic or diastolic murmurs, systolic ejection click, and variations in amplitude or frequency of the normal heart sounds (the first heart sound, S1; and the second heart sound, S2). Conventional stethoscopic examination of the heart may reveal gross abnormalities of the heart sounds, but more subtle abnormalities are difficult to identify using the stethoscope. Use of phonocardiography or apex cardiography can enhance diagnostic capabilities but attempts by other practitioners to develop computer-generated average wave forms (the abovementioned Sarkady et al. and Yanaga et al. articles) have not provided the time-domain analyses as suggested for each of multiple frequency bands in the present invention.

Conventionally, personnel performing heart sound analysis filter the sound signal into a predetermined frequency range prior to recording the sound signal, thus potentially losing valuable data in other frequency ranges. According to the present invention, the full range of frequencies is recorded so that any of a large number of frequencies can be evaluated during the post-recording analysis.

The present invention permits simple and precise measurement of sound amplitude within specific frequency bands associated with particular types of abnormality. Specifically, it allows evaluation of the infrasonic spectrum as well as the spectrum to which the human ear is responsive; it has been shown that the majority of the sound energy generated by the heart is in the infrasonic spectrum and thus is inaccessible to analysis by use of the stethoscope or phonocardiography. Thus, it can serve as a more sensitive method for diagnosis of disease associated with abnormal sound generation within a narrow frequency band.

This invention also permits clarification of the underlying etiology in certain cardiac arrhythmias not adequately characterized by electrocardiography (ECG). The ECG analysis is frequently unable to differentiate between a ventricular tachycardia and a supraventricular tachycardia with QRS aberration; since these two arrhythmias are associated with different patterns of heart sounds, the present invention can aid in differentiating those conditions, and thus in identifying if the patient has the dangerous condition of ventricular tachycardia or the more benign condition of supraventricular tachycardia.

Similarly, an extended time recording can differentiate between single ventricular premature beats and single supraventricular premature beats with QRS aberration.

The present invention also permits sophisticated additional processing of signal averaged heart sounds which provides an average wave form summating the sounds of multiple cardiac cycles. This is possible by computer processing of digitized "envelope" amplitudes. The normal heart sounds consist of the first heart sound (S1) and the second heart sound (S2). Patients with cardiac failure may also have a third heart sound (S3) or a fourth heart sound (S4) and other abnormal sounds such as clicks or murmurs. Each normal or abnormal heart sound signal is concentrated within a fairly narrow band of the sound spectrum, and thus is more clearly identified by sound analysis within this frequency band. According to the present invention, the computer automatically calculates novel measures from the signal averaged heart sound data, including the S1-S2/S2-S1 ratio, and the amplitudes, volumes (Area Under the Curve; AUC) and widths (at 50% of peak) of S1, S2, S3 and S4. The computer calculates and displays on the average wave form graph (as shown by dots in FIG. 3) the Standard Error of the Mean (SEM) for each point in the average wave form to provide a measure of the precision of the estimates of average amplitude. These signal averaging techniques may be applied to any individual frequency bands evaluated or to a combination of frequency bands.

An important limitation of current average wave form techniques is that no assessment is made of the accuracy of the average wave form in representing the underlying activity of the sound emanating structure; thus small spikes in the average wave form cannot be reliably differentiated from random variations. Use of the Standard Error of the Mean as well as the Mean for the average wave form allows differentiation from random variations—since a real event will show reproducibility from cycle to cycle and thus show a small SEM.

Figure 3A:
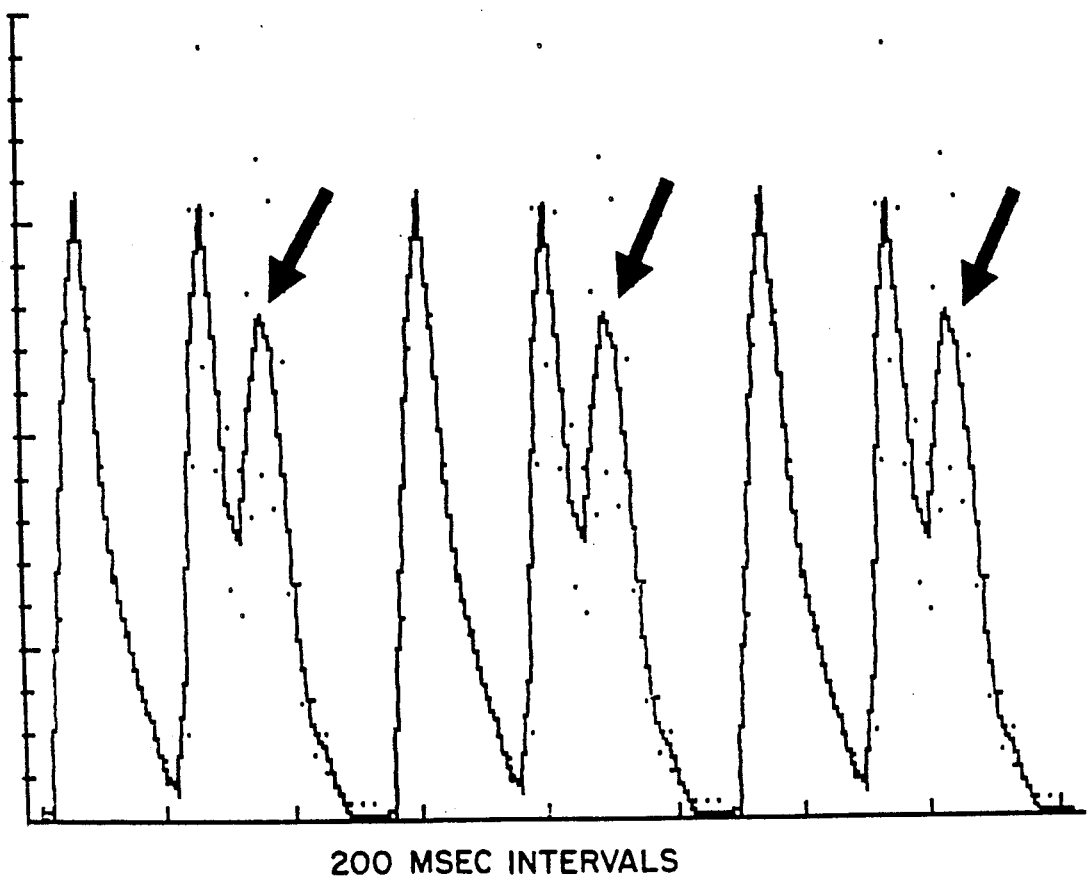
FIG. 3a represents an average wave form computer analysis of a patient with a third heart sound.
Figure 3B:
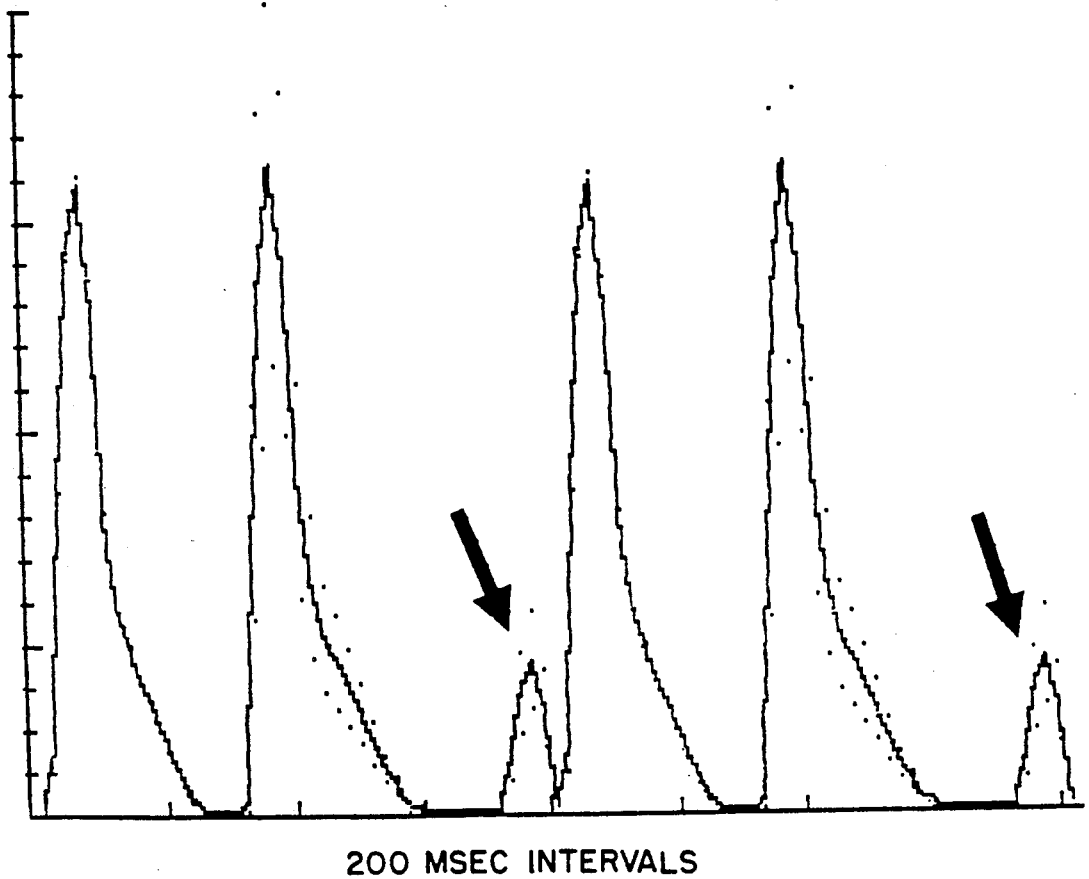
FIG. 3b represents an average wave form computer analysis of a patient with a fourth heart sound.
Figure 3C:
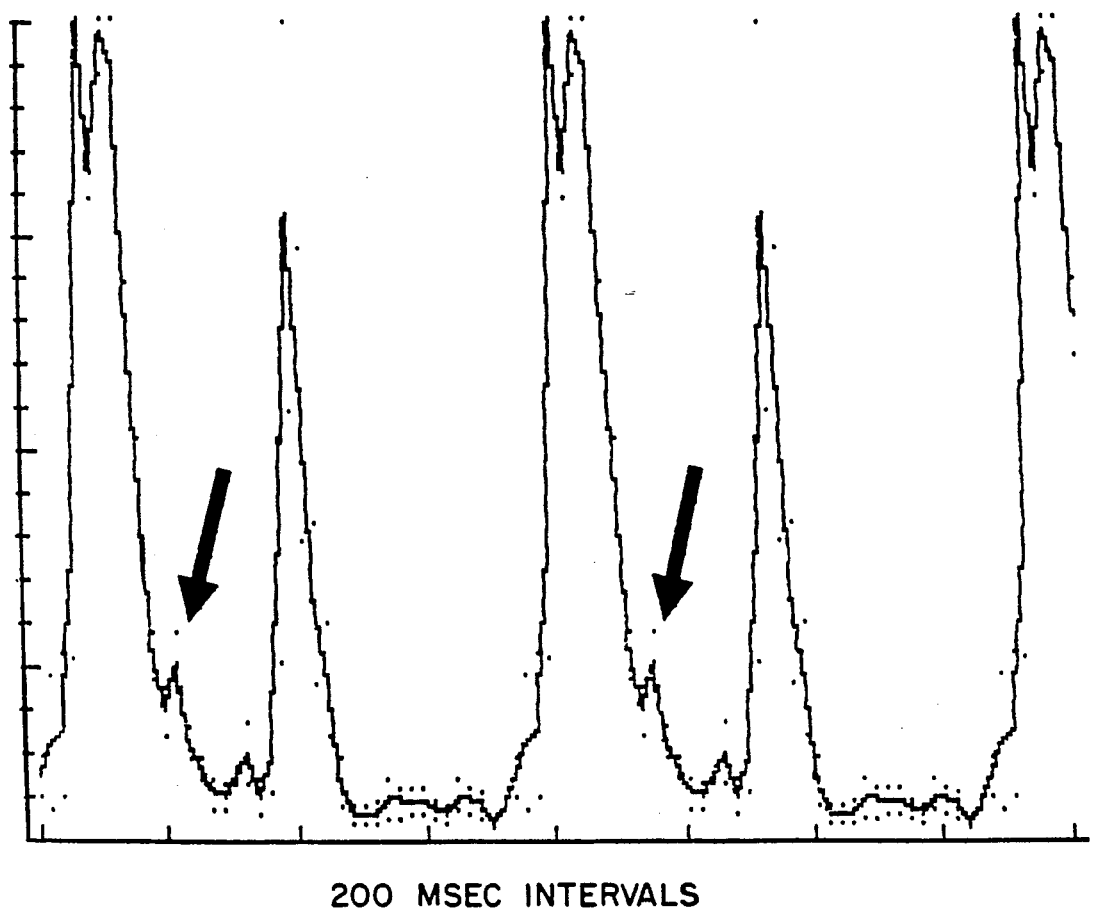
FIG. 3c represents an average wave form computer analysis of a patient with a systolic ejection murmur.

FIG. 3 represents average wave form computer analyses (80-160 Hz frequency range) for a patient with a third heart sound (FIG. 3A), a patient with a fourth heart sound (FIG. 3B), and a patient with a systolic ejection murmur (FIG. 3C). Use of the average wave form technique in which values from multiple cardiac cycles (e.g. 50-100 cycles) are averaged improves the signal to noise ratio and this allows identification of more subtle heart disease manifestations than can be achieved by conventional non-computer-assisted auscultatory or phonocardiographic techniques; in addition, the novel computer algorithms utilized provide automated and novel calculations of frequency and time domain characteristics not possessed by other computer-assisted methods.

EXAMPLE 3

Analysis of Respiratory Sounds

Figure 4:
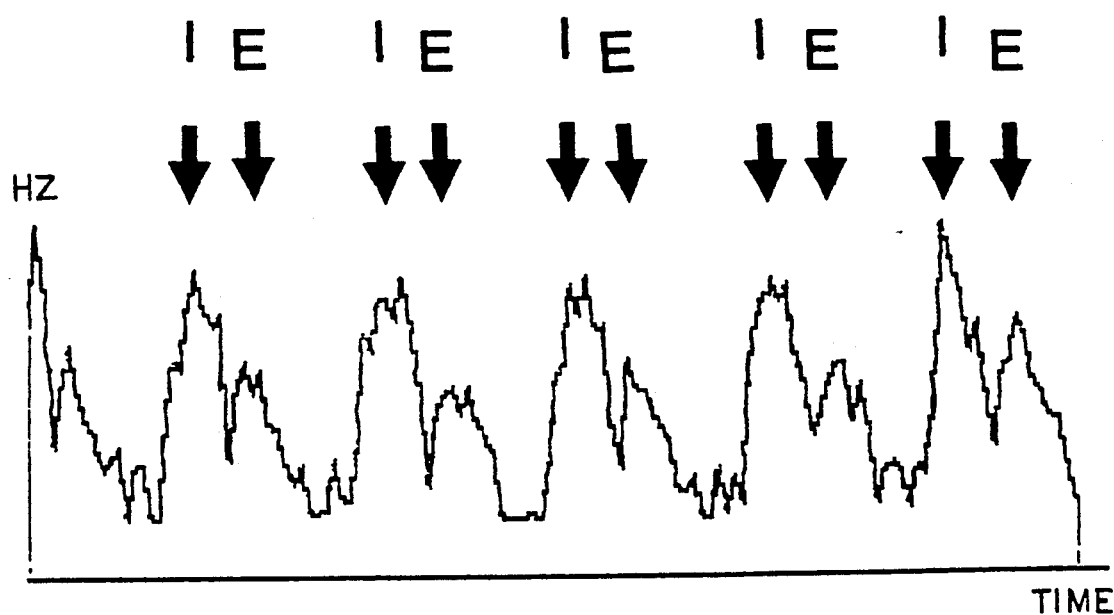
FIG. 4 represents a recording of breath sounds in a normal volunteer.

FIG. 4 is a paper chart recording of breath sounds in a normal volunteer. Similar average wave form analysis to that shown in FIG. 3 assists in identification of subtle manifestations of the disease associated with abnormal breath sounds.

In FIG. 4, amplitude is on ordinate and time is on abscissa. I=Peak Sound Intensity With Inspiration. E=Peak Sound Intensity With Expiration. Sound Frequency band width=315-16,000 Hz.

It is to be appreciated that the above examples are illustrative, and that somewhat different methods of recording the sound signals and somewhat different methods of performing the computer analysis of the data may be appropriate depending on the disease or syndrome under evaluation.

With reference to the Computer Program Listings showing computer listing I, it has identified means for calculating an average wave form. Identification of the peaks (e.g. of the first and second heart sounds) is made to provide two linked data streams, one consisting of the digitized sound amplitudes and the other being a blank data stream in which is inserted (by computer or human identification) a signal representing the amplitudes associated with the peak first derivative of the upstroke of the amplitude of the peaks. It is then possible to calculate mean values and standard errors of the means for each time point at, before, or after the peak.

| In FIG. 3A: | |
|---|---|
| PATIENT IDENTIFICATION: | Third heart sound in CHF patient |
| ACTIVITY LEVEL: | Rest |
| DIAGNOSIS: | Chronic heart failure |
| HEART RATE (BPM): 111 | S1-S2/S2-S1 RATIO: 0.57 |
| AMPLITUDE ENTIRE CARDIAC CYCLE: | MEAN 37.2 MINIMUM 0 MAXIMUM 144 |
| PEAK AMPLITUDE: | WIDTH AT 50% OF PEAK AMPLITUDE: |
| S1: 144 | S1: 36 msec |
| S2: 142 | S2: 44 msec |
| MEAN SOUND VOLUME INDEX: | S3 AND S4 INDICES (MEAN ± SEM) |
| S1: 56 | S3: 116 (±2.7) |
| S2: 53 | S4: 0 (±0.0) |
| In FIG. 3B: | |
| PATIENT IDENTIFICATION: | Patient with fourth heart sound |
| ACTIVITY LEVEL: | Rest |
| DIAGNOSIS: | Fourth Heart Sound |
| HEART RATE (BPM): 74 | S1-S2/S2-S1 RATIO: 0.6 |
| AMPLITUDE ENTIRE CARDIAC CYCLE: | MEAN 28.1 MINIMUM 0 MAXIMUM 151 |
| PEAK AMPLITUDE: | WIDTH AT 50% OF PEAK AMPLITUDE: |
| S1: 147 | S1: 36 msec |
| S2: 151 | S2: 32 msec |
| MEAN SOUND VOLUME INDEX: | S3 AND S4 INDICES (MEAN ± SEM) |
| S1: 55.9 | S3: 0 (±0) |
| S2: 54.7 | S4: 35 (±1.4) |
| In FIG. 3C: | |
| PATIENT IDENTIFICATION: | Patient with systolic ejection murmur |
| ACTIVITY LEVEL: | Rest |
| DIAGNOSIS: | Systolic Ejection murmur |
| HEART RATE (BPM): 81.2 | S1-S2/S2-S1 RATIO: 0.78 |
| AMPLITUDE ENTIRE CARDIAC CYCLE: | MEAN 33.5 MINIMUM 2 MAXIMUM 190 |
| PEAK AMPLITUDE: | WIDTH AT 50% OF PEAK AMPLITUDE: |
| S1: 190 | S1: 90 msec |
| S2: 143 | S2: 29 msec |
| MEAN SOUND VOLUME INDEX: | S3 AND S4 INDICES (MEAN ± SEM) |
| S1: 100.1 | S3: 5 (±0.9) |
| S2: 38.7 | S4: 6 (±0.8) |

Further, means for generating the time/amplitude plots is identified in the computer listings I provided. Graphic displays are generated, as shown in the examples in FIGS. 2-4.

Means for generating the frequency/amplitude plots is also identified in the computer listings I provided. An example of the graphic display is shown in FIG. 2b constituting a time/amplitude plot broken down by frequency group; other displays utilize a frequency/amplitude plot 6 with amplitude on the ordinate and frequency on the abscissa.

Displays of the amplitude, volume, width and frequency pattern of the peaks are illustrated in FIGS. 2-4 and in the program listings I provided.

Processing of bowel sound data uses the above-described procedures, using combinations of frequency bands and average wave form procedures suitable for the more variable characteristics of bowel sound data. The sound signal is generated using a larger microphone (Narco Biosystems ® model 705-0016) and using a longer duration of sound recording (typically 15 minutes) compared with recording of heart sounds.

The method according to the present invention is a new procedure which:

a) has shown to be clinically useful in the diagnosis of patients with disease associated with abnormal body sound production, and in serial evaluation of the severity of disease in a given patient, and b) provides more extensive information on abnormal body sound production than conventional methods, thereby enhancing the value of body sound evaluation in diagnosing and monitoring human disease.

There has been disclosed heretofore the best embodiment of the invention presently contemplated. However, it is to be understood that various changes and modifications may be made thereto without departing from the spirit of the invention.

What is claimed is:

1. A system for evaluation of a human disease associated with abnormal body sound production from body multiple organ systems, the system comprising a microphone device placed in contact with a patient's body; means for generating and amplifying an analog sound signal received from said microphone device; as frequency analyzer connected to said generating and amplifying means and including first means for separating the sound signal into various frequency bands in infrasonic and audible spectrums, second means for determining a sound amplitude in each frequency band, and means for digitizing the analog sound signal to obtain digital signals; and a computer for receiving said digital signals from said frequency analyzer and performing an average wave form analysis of said signals so as to provide time averaged calculation of body sound data.

2. A system as set forth in claim 1, and further comprising means for generating time/amplitude plots arranged to provide evaluation of a human disease.

3. A system as set forth in claim 1, and further comprising means for generating frequency/amplitude plots arranged to provide evaluation of a human disease.

4. A system as set forth in claim 1, and further comprising means for identifying peaks in the body sound data arranged to provide amplitude, volume, width, and frequency patterns of the peaks.

5. A system as set forth in claim 1, wherein said frequency analyzer and said computer are adapted for analyzing bowel sounds and arranged to provide information for diagnosis and monitoring of certain diseases of the gastro-intestinal tract.

6. A system as set forth in claim 1, wherein said generating means includes an electronic amplifier connected to said microphone device via a cable.

7. A system as set forth in claim 1, wherein said separating means includes a bank of analog filters.

8. A system as set forth in claim 1, wherein said digitizing means includes an analog-to-digital converter.

9. A system as set forth in claim 1, wherein said computer is arranged so as to perform said analysis in the infrasonic range.

* * * * *